United States Patent [19]

Tomita et al.

[11] Patent Number: 5,428,016

[45] Date of Patent: Jun. 27, 1995

[54] ANTIMICROBIAL PEPTIDE AND ANTIMICROBIAL AGENT

[75] Inventors: Mamoru Tomita, Kanagawa; Kozo Kawase; Mitsunori Takase, both of Saitama; Wayne R. Bellamy, Kanagawa; Koji Yamauchi, Kanagawa; Hiroyuki Wakabayashi, Kanagawa; Yukio Tokita, Kanagawa, all of Japan

[73] Assignee: Morinaga Milk Industry Co., Ltd., Japan

[21] Appl. No.: 851,941

[22] Filed: Mar. 13, 1992

[30] Foreign Application Priority Data

Mar. 13, 1991 [JP] Japan .................... 3-048196
Apr. 24, 1991 [JP] Japan .................... 3-094492
Apr. 24, 1991 [JP] Japan .................... 3-094493

[51] Int. Cl.$^6$ .................... A61K 37/00; A61K 37/02; C07K 5/00; C07K 7/00
[52] U.S. Cl. .................... 514/15; 514/16; 514/17; 530/327; 530/328; 530/329; 530/330
[58] Field of Search ............... 530/327, 328, 329, 330; 514/15, 16, 17

[56] References Cited

FOREIGN PATENT DOCUMENTS 9119512 12/1991 WIPO .................... A61K 37/02

OTHER PUBLICATIONS

Raha et al., *Blood*, vol. 72, No. 1, pp. 172–178, 1988.

*Primary Examiner*—Lester L. Lee
*Assistant Examiner*—A. M. Davenport
*Attorney, Agent, or Firm*—Wenderoth, Lind & Ponack

[57] ABSTRACT

An antimicrobial peptide containing at least the following amino acid sequence, or a derivative thereof, an antimicrobial agent containing said antimicrobial peptide or a derivative thereof as active components at a concentration of at least 1 $\mu$M, an antimicrobial composition containing said antimicrobial peptide or a derivative thereof, and a method for processing products which uses the antimicrobial agent containing at least said antimicrobial peptide or a derivative thereof:

A—X—A (where, A is an arginine residue or a lysine residue; and X is an amino acid sequence comprising at least from three to nine arbitrary amino acid residues other than cysteine residues.)

4 Claims, 3 Drawing Sheets

| SAMPLE NO. | ADDED QUANTITY (μM) AND INHIBITORY RATE (%) | | | | | | | |
|---|---|---|---|---|---|---|---|---|
| | 0.5 | 1 | 2 | 5 | 10 | 20 | 60 | 100 |
| 1 | 0 | 60 | 97 | 100 | 100 | 100 | 100 | 100 |
| 2 | 0 | 61 | 79 | 100 | 100 | 100 | 100 | 100 |
| 3 | 0 | 35 | 60 | 79 | 95 | 98 | 100 | 100 |
| 4 | 0 | 50 | 73 | 88 | 95 | 100 | 100 | 100 |
| 5 | 0 | 21 | 48 | 75 | 89 | 95 | 100 | 100 |
| 6 | 0 | 65 | 100 | 100 | 100 | 100 | 100 | 100 |
| 7 | 0 | 30 | 87 | 100 | 100 | 100 | 100 | 100 |
| 8 | 0 | 42 | 72 | 83 | 91 | 95 | 100 | 100 |
| 9 | 0 | 25 | 46 | 63 | 80 | 90 | 100 | 100 |
| 10 | 0 | 28 | 55 | 81 | 90 | 97 | 100 | 100 |
| 11 | 0 | 65 | 100 | 100 | 100 | 100 | 100 | 100 |
| 12 | 0 | 30 | 87 | 100 | 100 | 100 | 100 | 100 |
| 13 | 0 | 42 | 72 | 83 | 91 | 95 | 100 | 100 |
| 14 | 0 | 25 | 46 | 63 | 80 | 90 | 100 | 100 |
| 15 | 0 | 28 | 55 | 81 | 90 | 97 | 100 | 100 |

FIG. 1

| SAMPLE NO. IN THE AGENT | VIABLE COUNT/g (CONTROL) | | | |
|---|---|---|---|---|
| | 0 HR. | 12 HRS. | 24 HRS. | 36 HRS. |
| 1 | $1.3 \times 10^3$ ($1.3 \times 10^3$) | $1.5 \times 10^3$ ($2.9 \times 10^4$) | $1.7 \times 10^3$ ($3.1 \times 10^5$) | $2.0 \times 10^3$ ($4.8 \times 10^5$) |
| 6 | $1.3 \times 10^3$ ($1.3 \times 10^3$) | $1.4 \times 10^3$ ($3.2 \times 10^4$) | $1.7 \times 10^3$ ($2.7 \times 10^5$) | $2.1 \times 10^3$ ($5.1 \times 10^5$) |

FIG. 2

| AGENT | VIABLE COUNT/g | | | | |
|---|---|---|---|---|---|
| | 0 DAY | 1 DAY | 2 DAYS | 3 DAYS | 4 DAYS |
| THE PRESENT INVENTION | <100 | <100 | <100 | <100 | $1.5 \times 10^2$ |
| CONTROL | <100 | <100 | $5.5 \times 10^2$ | $2.4 \times 10^3$ | $7.8 \times 10^8$ |

FIG. 3

| SAMPLE NO. | MINIMUM INHIBITORY CONCENTRATION ($\mu$M) | | | |
|---|---|---|---|---|
| | L M | S A | P A | K P* |
| 1 | 50 | 25 | —** | — |
| 2 | 6 | 25 | — | — |
| 3 | 100 | 250 | — | — |
| 4 | 50 | 250 | — | — |
| 5 | 50 | 25 | — | — |
| 6 | 25 | 50 | — | — |
| 7 | 12 | 25 | — | — |
| 8 | 25 | 100 | — | — |
| 9 | 25 | 25 | — | — |
| 10 | 50 | 100 | — | — |
| 11 | 1.5 | 3 | 6 | 25 |
| 12 | 1.5 | 3 | 6 | 25 |
| 13 | 6 | 12 | 50 | 50 |
| 14 | 6 | 12 | 25 | 50 |
| 15 | 3 | 6 | 25 | 50 |
| 16 | 12 | 100 | — | — |
| 17 | 3 | 6 | — | — |
| 18 | 1.5 | 3 | 3 | 12 |

NOTE )  *: CULTURED AT 30°C
 **: NOT TESTED

ANTIMICROBIAL PEPTIDE AND ANTIMICROBIAL AGENT

FIELD OF THE INVENTION

The present invention concerns an antimicrobial peptide and an antimicrobial agent. More specifically, it concerns an antimicrobial agent and an antimicobial composition containing a novel antimicrobial peptide or a derivative of this peptide, as active components, in addition to a method for treating products which uses this antimicrobial agent.

In the specification of the present invention, the amino acids and peptides are represented by the abbreviations employed by IUPAC-IUB Committee on Biochemical Nomenclature, such as the following abbreviations.

Ala-: L-Alanine residue
Arg-: L-Arginine residue
Asn-: L-Asparagine residue
Asp-: L-Aspartic acid residue
Cys-: L-Cysteine residue
Gln-: L-Glutamine residue
Glu-: L-Glutamic acid residue
Gly-: Glycine residue
His-: L-Histidine residue
Ile-: L-Isoleucine residue
Leu-: L-Leucine residue
Lys-: L-Lysine residue
Mct-: L-Methionine residue
Phe-: L-Phenylalanine residue
Pro-: L-Proline residue
Ser-: L-Serine residue
Thr-: L-Threonine residue
Trp-: L-Tryptophan residue
Tyr-: L-Tyrosine residue
Val-: L-Valine residue

PRIOR ART

Numerous inventions concerning peptides or their derivatives which possess antimicrobial properties against various microorganisms have so far been reported. Examples include a phosphonotripeptide (Japanese Patent Provisional Publication No. 106689/82), a phosphonodipeptide derivative (Japanese Patent Provisional Publication No. 13594/83) and a cyclic peptide derivative (Japanese Patent Provisional Publication No. 213744/83) effective against gram-positive and gram-negative bacteria, a peptide demonstrating an antimicrobial and antiviral action (Japanese Patent Provisional Publication No. 51247/84), a polypeptide effective against yeast (Japanese Patent Provisional Publication No. 130599/85), a saccharaaropeptide derivative effective against gram-positive bacteria (Japanese Patent Provisional Publication No. 172998/85, Japanese Patent Provisional Publication No. 251699/86, Japanese Patent Provisional Publication No. 44598/88, an oligopeptide effective against gram-positive bacteria (Japanese Patent Provisional Publication No. 22798/87), a peptidal antibiotic substance (Japanese Patent Provisional Publication No. 51697/87, Japanese Patent Provisional Publication No. 17897/88) as well as an antimicrobial peptide extracted from blood cells of North American king crabs (Japanese Patent Provisional Publication No. 53799/90) and an antimicrobial peptide isolated from blood lymph of honeybees (Japanese Patent Provisional Publication No. 500084/90).

On the other hand, lactoferrin (hereinafter referred to as "LF"), which is a natural iron-binding protein contained in tears, saliva, peripheral blood, milk etc. is known to demonstrate an antimicrobial activity against Escherichia coli, Candida, Clostridium and other harmful microorganisms (Journal of Pediatrics, Vol. 94, p. 1, 1979).

The inventors of the present invention, in planning to cheaply isolate from nature a substance which possesses strong antimicrobial properties, which has no undesirable side effects (such as antigenicity) and is heat-resistant, focused on whey, a by-product of cheese manufacturing, and conducted research regarding the antimicrobial properties of LP contained in it. Surprisingly, they discovered that catabolites of LF produced by acid hydrolysis or by enzymatic cleavage of this protein have stronger antimicrobial properties and are more heat resistant than non-hydrolyzed LF, and have succeeded to isolate and synthesize potent antimicrobial peptides possessing specific amino acid sequences, and have filed a patent application (Ser. No. 07/755,161). Previously, the amino acid sequences of these novel antimicrobial peptides have not been sufficiently understood, however, and, therefore, the development of an effective antimicrobial agent had not yet been achieved.

SUMMARY OF THE INVENTION

The objective of the present invention is to provide a novel antimicrobial peptide or a derivative thereof having a specific amino acid sequence which can be isolated from LF hydrolysate or chemically synthesized, and an antimicrobial agent, and an antimicrobial composition containing this peptide or its derivative as an active component, and a method for treating products which uses this antimicrobial agent.

The present invention provides:

(1) an antimicrobial peptide containing at least the following sequence, or a derivative thereof, (2) an antimicrobial agent containing an antimicrobial substance selected from the group consisting of an antimicrobial peptide which contains at least the following sequence or a derivative thereof, and pharmaceutically or sitologically approved salts thereof, or a mixture thereof, as active components, (3) a method for treating products which uses this antimicrobial agent, and (4) an antimicrobial composition containing an antimicrobial substance selected from the group consisting of an antimicrobial peptide which contains at least the following sequence or a derivative thereof, and pharmaceutically or sitologically approved salts thereof, or a mixture thereof, as active components.

A—X—A (where, A is an arginine residue or a lysine residue; and X is an amino acid sequence comprising at least from three to nine arbitrary amino acid residues other than cysteine residues.)

BRIEF DESCRIPTION OF DRAWINGS

FIG. 1, Table 1 demonstrates samples No. 1 to 15 had an antimicrobial activity at concentrations of 1 uM, and a high antimicrobial activity within a range of 5 to 20 uM.

FIG. 2, Table 2 demonstrates proliferation of bacteria which was remarkably inhibited in the vegetable treated with the antimicrobial agent of the present invention. The figures in parenthesis represent values for the control.

FIG. 3, Table 3 demonstrates proliferation of bacteria which was remarkably inhibited in the vegetable treated with the antimicrobial agent of the invention.

FIG. 4, Table 4 demonstrates various microbial strains in the logarithmic phase of growth inoculated in a peptone medium.

DETAILED DESCRIPTION OF THE INVENTION

The antimicrobial peptide or the derivative thereof of the present invention may be prepared by enzymatic hydrolysis of bovine LF isolated by the conventional method from cow's milk or a commercially available LF. The antimicrobial peptide derivatives are those derivatives having minor amino acid partial substitutions or additions which do not abolish the antimicrobial properties of the peptide.

Alternatively, the antimicrobial peptide of the present invention can be chemically synthesized, and an example of chemical synthesis of the peptide is as follows. Using an automated peptide synthesizer (such as the one manufactured by Pharmacia LKB Biotechnology Co., LKB Biolynk 4170), the peptide is synthesized following the solid-phase peptide synthesis method of Sheppard et al. (Journal of Chemical Society Perkin I, p. 538, 1981). N,N'-dicyclohexylcarbodiimide is added to amino acids whose amine functional groups are protected by 9-fluorenylmethoxycarbonyl (Fmoc) groups (hereinafter referred to as "Fmoc-amino acid") and anhydrides of the desired amino acids are produced, and these Fmoc-amino acid anhydrides are used for synthesis. In order to produce a peptide chain, an Fmoc-amino acid anhydride corresponding to the C-terminal amino acid residue is fixed to Ultrosyn A resin (manufactured by Pharmacia LKB Biotechnology Co.) through the carboxyl group thereof, using dimethylaminopyridine as a catalyst. Next, the resin is washed with dimethylformamide containing piperidine, and the protecting group of the amine functional group of the C-terminal amino acid is removed. Next, an Fmoc-amino acid anhydride corresponding to the amino acid residue which is second from the C-terminal of the amino acid sequence of the desired peptide is coupled to the unprotected amine functional group of the first amino acid fixed to the resin through the above-mentioned C-terminal amino acid residue. Subsequently the successive desired amino acids are fixed in the same manner. After coupling of all the amino acids is completed and the peptide chain of the desired amino acid sequence is formed, the protective groups other than acetoamidomethyl are removed and the peptide is released with a solvent [composed of, for example, 94% (weight. the same hereinafter unless otherwise indicated) trifluoroacetic acid, 5% phenol and 1% ethandiol], and the peptide is purified using high-performance liquid chromotography.

As an example of the antimicrobial peptide derivative of the present invention, a peptide having an amide at the carboxyl end is prepared as follows: fixing sequentially amino acid residues in the same manner as in the example mentioned above except for using Ultrosyn B resin (manufactured by Pharmacia LKB Biotechnology Co.); after the total completion of coupling of amino acid and the resultant formation of a peptide chain having a desired amino acid sequence, eliminating the protecting groups other than acetoamidemethyl by means of a solvent which comprises 94% trifuloroacetic acid, 5% phenol, and 1% ethandiol; then isolating peptides from the resin by means of a saturated ammonia/methanol solvent; and purifying peptides using high-performance liquid chromatography.

The antimicrobial peptide so obtained, the pharmaceutically or sitologically approved salts thereof, or a mixture of at least two of the above, is included as active components at a concentration of at least 1 micromole per kg and preferably 5 to 20 micromoles per kg, in order to obtain the antimicrobial agent or the antimicrobial composition of the present invention. Also, in the case of using the antimicrobial peptide derivative, the antimicrobial agent or composition can be obtained in the same manner as described above.

The antimicrobial peptide or derivative thereof of the present invention can be administered to humans or to animals without further modifications, can be used in food products, medicinal pharmaceutical products (such as eye medications, mastitis medications, diarrhea medications and athlete's foot medications), non-medicinal pharmaceutical products (such as mouth washes, antiperspirants and hair tonics), various cosmetic products (such as hair conditioners), various tooth-brushing products (such as toothpastes and toothbrushes), various feminine hygiene products, various baby products (such as diapers), various geriatric products (such as denture cement and diapers), various cleaning agents (such as soaps, medicinal soaps, shampoos, rinses, laundry detergents, kitchen detergents and house detergents), various sterilized products (such as sterilized kitchen paper and sterilized toilet paper), feed and materials which serve as raw materials of the above, and they can also be added to, compounded with, sprayed onto, adhered to or used for coating or impregnation of any and all products wherein prevention or inhibition of microbial proliferation is generally desired.

The antimicrobial peptide or derivative thereof of the present invention can be used individually or concomitantly with other antimicrobial agents for treating any and all products wherein prevention or inhibition of microbial proliferation is generally desired, for example, food products, medicinal pharmaceutical products (such as eye medications, mastitis medications, diarrhea medications and athlete's foot medications), non-medicinal pharmaceutical products (such as mouth washes, antiperspirants and hair tonics), various cosmetic products (such as hair conditioners), various tooth-brushing products (such as toothpastes and toothbrushes), various feminine hygiene products, various baby products (such as diapers), various geriatric products (such as denture cement and diapers), various cleaning agents (such as soaps, medicinal soaps, shampoos, rinses, laundry detergents, kitchen detergents and house detergents), various sterilized products (such as sterilized kitchen paper and sterilized toilet paper), feed and materials which serve as raw materials of the above.

Next, the present invention will be described in detail by means of Experiments.

EXPERIMENT 1

This experiment was performed in order to study the antimicrobial activity of an antimicrobial peptide.

(1) Sample preparation

Samples of Nos. 1 to 15 were chemically synthesized using the same methods as in Examples 1 to 15, respectively.

(2) Experimental method

1. Preparation of a pre-incubation solution

One platinum loop was collected from a stock slant of *Escherichia coli*, streaked on a standard agar medium (manufactured by Nissui Pharmaceutical Co.) and incubated under aerobic conditions for 16 hours at 37° C., the colines which grew on the surface of the standard agar medium were collected using a platinum loop, suspended in sterilized physiological saline solution, the turbidity was measured using a spectrophotometer (manufactured by Hitachi Manufacturing Co.) and adjusted to 0.1 (O.D.; 660 nm) and a pre-incubation solution was prepared.

2. Preparation of a basal medium

Bactocasitone (manufactured by Difco Laboratory Co.) was dissolved at a concentration of 1% in purified water, the pH was adjusted to 7.0 with 1M sodium hydroxide, the solution was sterilized at 115° C. for 15 minutes and a basal medium (liquid medium) was prepared.

3. Preparation of the test media and of the control medium

Each sample was dissolved at a concentration of 0.01% in purified water, sterilization was performed by using a sterilization filter (manufactured by Advantek Co.) and test media, prepared by adding samples at concentrations of 0.5, 1, 2, 5, 10, 20, 50 and 100 micromol ($\mu$M) to the basal medium, as well as a control medium with no added samples, were prepared.

4. Antimicrobial activity test

The above-mentioned pre-incubation solution was inoculated into the above-mentioned test media and the control medium at a concentration of 1%, cultured under aerobic conditions for 16 hours at 37° C., the tribudities of the culture media were measured using the above-mentioned method and the rate of inhibition of *E. coli* proliferation was calculated according to the following formula.

$$\text{rate of inhibition of proliferation (\%)} = 100 \ (1-A/B)$$

wherein A is the difference in turbidity of the test culture medium (the difference between the turbidity of the test culture medium after 16 hours of culture and the turbidity of the test culture medium before the culturing) and B is the turbidity of the control medium (the difference between the turbidity of the control culture medium after 16 hours of culture and the turbidity of the control culture medium before the culturing). The percentages of the rate of inhibition of proliferation are not in weight (same hereinafter).

(3) Results

The results of this experiment are shown in Table 1. As is clear from Table 1, all the samples Nos. 1 to 15 had an antimicrobial activity at concentration of 1 $\mu$M, and a high antimicrobial activity within a range of 5 to 20 $\mu$M. At concentrations over 50 $\mu$M, such increase in concentration did not lead to increased antimicrobial activity. Antimicrobial activity of each peptide is therefore available at a concentration of at least 1 $\mu$M, and more preferably, within a range of 5 to 20 $\mu$M. Antimicrobial activity within this quantity range is almost equal to that of aminobenzylpenicillin.

Antimicrobial activity was tested also for peptides having amino acid sequences other than those of the above-mentioned samples Nos. 1 to 15, derivatives thereof and salts thereof, and similar results were obtained.

EXPERIMENT 2

This experiment was performed in order to determine the amino acid sequence of the antimicrobial peptide used in Experiment 1.

The peptides of sample Nos. 1 to 15 used in Experiment 1 were hydrolyzed by 6N hydrochloric acid and the amino acid compositions were analyzed by conventional methods, using an amino acid analyzer. Given cycles of Edman's degradation were performed on each sample, using a gas-phase sequencer (manufactured by Applied Biosystems Co.), and sequences of amino acid residues was determined.

As a result it was determined that this peptide consisted of 5, 6 or 11 amino acid residues, and formed the following amino acid sequence.

Sample No. 1: Arg-Trp-Gln-Trp-Arg (SEQ ID NO. 1)
Sample No. 2: Arg-Arg-Gln-Trp-Arg (SEQ ID NO. 2)
Sample No. 3: Lys-Val-Ser-Trp-Arg (SEQ ID NO. 3)
Sample No. 4: Arg-Asn-Met-Arg-Lys (SEQ ID NO. 4)
Sample No. 5: Arg-Trp-Gln-Glu-Lys (SEQ ID NO. 5)
Sample No. 6: Arg-Arg-Trp-Gln-Trp-Arg (SEQ ID NO. 6)
Sample No. 7: Arg-Arg-Arg-Gln-Trp-Arg (SEQ ID NO. 7)
Sample No. 8: Lys-Thr-Val-Ser-Trp-Arg (SEQ ID NO. 8)
Sample No. 9: Lys-Arg-Asn-Met-Arg-Lys (SEQ ID NO. 9)
Sample No. 10: Arg-Trp-Gln-Glu-Met-Lys (SEQ ID NO. 10)
Sample No. 11: Lys-Thr-Arg-Arg-Trp-Gln-Trp-Arg-Met-Lys-Lys (SEQ ID NO. 11)
Sample No. 12: Lys-Ser-Arg-Arg-Arg-Gln-Trp-Arg-Met-Lys-Lys (SEQ ID NO. 12)
Sample No. 13: Lys-Thr-Val-Ser-Trp-Gln-Thr-Tyr-Met-Lys-Lys (SEQ ID NO. 13)
Sample No. 14: Lys-Thr-Phe-Gln-Trp-Gln-Arg-Asn-Met-Arg-Lys (SEQ ID NO. 14)
Sample No. 15: Lys-Thr-Leu-Arg-Trp-Gln-Asn-Glu-Met-Arg-Lys (SEQ ID NO. 15)

EXPERIMENT 3

This experiment was performed to study the antimicrobial effect of an antimicrobial agent containing the peptide of the present invention.

Commercially available primary-processed vegetable (known as "cut vegetable") in an amount of 100 g was immersed in an aqueous solution for 30 seconds, in which the antimicrobial peptide (sample No. 1 or 6) synthesized in the same manner as in Example 1 or 6 was added at a concentration of 10 $\mu$M. After sufficiently eliminating water, the vegetable was held at 5° C., and the viable count was measured by the conventional method along with time lapse. Vegetable immersed in city water with no antimicrobial peptide served as control.

The results of this experiment are shown in Table 2. In this table, the figures in parentheses represent values for control. As in clear from Table 2, proliferation of bacteria was remarkably inhibited in the vegetable treated with the antimicrobial agent of the present invention. Almost the same results were obtained also for antimicrobial peptides synthesized in the same manner as in the other Examples and the salts thereof.

EXPERIMENT 4

This experiment was performed to study the antimicrobial effect of an antimicrobial agent containing the antimicrobial peptide derivative of the present invention.

Commercially available primary-processed vegetable (known as "cut vegetable") in an amount of 100 g was immersed in an aqueous solution for 30 seconds, in which the antimicrobial peptide derivative (sample No. 18) synthesized in the same manner as in Example 18 was added at a concentratin of 20 $\mu$M. After sufficiently eliminating water, the vegetable was held at 5° C., and daily changes in the viable count were measured by the conventional method. Vegetable immersed in city water with no antimicrobial peptide derivative served as control.

The results of this experiment are shown in Table 3. As is clear from Table 3, proliferation of bacteria was remarkably inhibited in the vegetable treated with the antimicrobial agent containing the peptide derivative of the present invention. Similar results were obtained also for antimicrobial peptide derivatives synthesized in the same manner as in the other Examples and the salts thereof.

EXPERIMENT 5

This experiment was performed to study the preservative effect in foods mixed with the antimicrobial peptide of the present invention.

Milk was pasteurized at 65° C. for 30 minutes and poured separately into test tubes to an amount of 10 ml each. The antimicrobial peptide (Sample No. 2 or 7) synthesized in the same manner as in Example 2 or 7 was added to the milk at a concentration of 30 $\mu$M, and the mixture was uniformly mixed, and closely sealed. Milk in a sealed test tube with no antimicrobial peptide served as control. All the test tubes were held at 25° C., and the number of days required for the milk to solidify was measured.

As a result, while all the milk containing the antimicrobial peptide solidified in ten days, the control solidified in two days. This suggests that the antimicrobial peptides of the present invention largely retarded solidification of milk. An organoleptic test carried out on the tested milk and the control before preservation showed no difference in flavor or in exterior view between the two groups. Similar results were obtained for antimicrobial peptides synthesized in the same manner as in the other Examples and the derivatives thereof.

EXPERIMENT 6

This experiment was performed to study the antimicrobial spectrum of the antimicrobial peptides and the derivatives thereof of the present invention.

(1) Sample preparation

The antimicrobial peptides (samples Nos. 1 to 15) were prepared using the same methods as in Examples 1 to 15, and antimicrobial peptide derivatives (samples Nos. 16 to 18) were prepared using the same methods as in Examples 16 to 18, and were sterilized by filtration using a 0.45 $\mu$m Millex filter prior to use.

(2) Experimental methods

Various microbial strains shown in Table 4 in the logarithmic phase of growth were inoculated in a peptone medium which consisted of 1% Bactopeptone (manufactured by Difco Laboratory Co.) at a cell concentration of $10^6$/ml, and 160 $\mu$l thereof were incubated for 17 hours at 37° C. (or 30° C.) using a 96-hole microtiter plate (manufactured by Falcon Co.). Each sample was added to each medium at a ratio of 0, 1.5, 3, 6, 12, 25, 50, 100, 125 or 250 $\mu$M. The growth of the various microorganisms in the various samples at various concentrations was studied by measuring the light absorption at 660 nm. The minimum concentration of the antimicrobial peptide which completely inhibited the growth of the various microorganisms was considered the minimum inhibitory concentration (MIC: $\mu$M).

The microorganisms used in this experiment are available from The Medical School Laboratories of Tokyo University (IID), Japanese Physicochemical Laboratories (JCM), Japanese International Dairy Federation (IDF), and the storage at the laboratory of the applicant (MMI).

(3) Results

The results of this experiment are shown in Table 4. As is clear from Table 4, the antimicrobial peptides of samples Nos. 1 to 5 showed an antimicrobial activity at concentrations of up to 250 $\mu$M against the tested Gram-positive bacteria, *Listeria monocytogenes* IDF 1b (represented by LM in the table) and *Staphylococcus aureus* JCM 2151 (represented by SA in the table), whereas samples Nos. 6 to 10 showed an antimicrobial activity at concentrations of up to 100 $\mu$M against these bacteria.

Sample No. 16 which is the derivative of sample No. 1 showed a strong antimicrobial activity about 2.5 to 4 times as high as that of sample No. 1, and sample No. 17 which is the derivative of sample No. 6 showed a strong antimicrobial activity about eight times as high as that of sample No. 6.

Furthermore, samples Nos. 11 to 15 showed an antimicrobial activity at concentrations of up to 12 $\mu$M against Gram-positive bacteria LM and SA, and showed an antimicrobial activity at concentrations of up to 50 $\mu$M against the tested Gram-negative bacteria, *Pseudomonas aeruginosa* MMI 603 (represented by PA in the table) and *Klebsiella pneumoniae* JCM 1662 T (represented by KP in the table).

Sample No. 18 which is the derivative of sample No. 11 showed a strong antimicrobial activity about twice as high as that of sample No. 11 against Gram-negative strains. This sample No. 18 showed also an antimicrobial activity at low concentrations of 6 $\mu$M and 3 $\mu$M, respectively, against *Escherichia coli* MMI 0111 and *Escherichia coli* IID 861 otherwisely tested.

In addition, virtually identical results were obtained with the other antimicrobial peptides of the present invention, other antimicrobial peptides derivatives and salts thereof.

EFFECTS OF THE INVENTION

Since the antimicrobial peptide or derivative thereof of the present invention possesses an antimicrobial activity which is considerably better than that of natural LF or LF hydrolysate and is effective against a wide range of microorganisms, it is suitable for a wide range of applications, and since it demonstrates an antimicrobial effect even in small amounts, it can be applied to food products etc. with hardly any effect on their flavor.

The present invention will now be explained in further detail by means of examples. Of course, the present invention is not limited to or by these examples.

EXAMPLE 1

A peptide was synthesized using an automated peptide synthesizer (manufactured by Pharmacia LKB Biotechnology Co., Trademark: LKB Biolynx 4710) in accordance with the solid-phase peptide synthesis method of Sheppard et al. (the Journal of Chemical Society Perkin I, p. 536, 1981).

N,N'-dicyclohexylcarbodiimide was added to amino acids whose the amine functional groups were protected by Fmoc groups and anhydrides of the desired amino acids were produced, and these Fmoc-amino acid anhydrides were used for synthesis. In order to produce a peptide chain, about 0.1 mmol of Fmoc-arginine anhydride corresponding to the C-terminal arginine residue was fixed to 1 g of Ultrosyn A resin (manufactured by Pharmacia LKB Biotechnology Co.) through the carboxyl group thereof, using dimethylaminopyridine as a catalyst. Next, the resin in an amount of 1 g was washed with dimethylformamide containing piperidine, and the protecting group of the amine functional group of the C-terminal amino acid was removed. The Fmoc-tryptophan anhydride corresponding to the second amino acid residue from the C-terminal was then coupled to the unprotected amine functional group of the above-mentioned arginine residue. Subsequently, glutamine, tryptophan and arginine were sequentially fixed in the same manner.

After the completion of coupling of all amino acids and formation of a peptide chain of the desired amino acid sequence, protecting groups other than acetoamidomethyl were removed and the peptide was released with a solvent comprising 94% trifluoroacetic acid, 5% phenol and 1% ethandiol, the peptide was purified by using high-performance liquid chromatography. This solution was concentrated and dried, and about 3 mg of peptide was obtained.

EXAMPLE 2

About 4 mg of a peptide having the amino acid sequence Arg-Arg-Gln-Trp-Arg was obtained in the same manner as in Example 1 except that the fourth amino acid residue from the C-terminal was replaced with arginine residue (SEQ ID NO. 2).

EXAMPLE 3

About 5 mg of a peptide having the amino acid sequence Lys-Val-Ser-Trp-Arg was obtained in the same manner as in Example 1 except that the third, the fourth and the fifth amino acid residues from the C-terminal were replaced with serine residue, valine residue and lysine residue, respectively (SEQ ID NO. 3).

EXAMPLE 4

About 4 mg of peptide having the amino acid sequence Arg-Asn-Met-Arg-Lys was obtained in the same manner as in Example 1 except that the first, the second, the third and the fourth amino acid residues from the C-terminal were replaced with lysine residue, arginine, methionine, and asparagine residues, respectively (SEQ ID NO. 4).

EXAMPLE 5

About 5 mg of a peptide having the amino acid sequence Arg-Trp-Gln-Glu-Lys was obtained in the same manner as in Example 1 except that the first and the second amino residues from the C-terminal were replaced with lysine residue and glutamic acid residue, respectively (SEQ ID NO. 5).

EXAMPLE 6

About 6 mg of a peptide having the amino acid sequence Arg-Arg-Trp-Gln-Trp-Arg was obtained in the same manner as in Example 1 except that an arginine residue was additionally fixed at the sixth position from the C-terminal (SEQ ID NO. 6).

EXAMPLE 7

About 4 mg of a peptide having the amino acid sequence Arg-Arg-Arg-Gln-Trp-Arg was obtained in the same manner as in Example 6 except that the fourth amino acid residue from the C-terminal was replaced with arginine residue (SEQ ID NO. 7).

EXAMPLE 8

About 6 mg of a peptide having the amino acid sequence Lys-Thr-Val-Ser-Trp-Arg was obtained in the same manner as in Example 6 except that the third, the fourth, the fifth and the sixth residues from the C-terminal were replaced with serine residue, valine residue, threonine residue and lysine residue, respectively (SEQ ID NO. 8).

EXAMPLE 9

About 5 mg of a peptide having the amino acid sequence Lys-Arg-Asn-Met-Arg-Lys was obtained in the same manner as in Example 6 except that the first, the second, the third, the fourth and the sixth amino acid residues from the C-terminal were replaced with lysine residue, arginine residue, methionine residue, asparagine residue and lysine residue, respectively (SEQ ID NO. 9).

EXAMPLE 10

About 7 mg of a peptide having the amino acid sequence Arg-Trp-Gln-Glu-Met-Lys was obtained in the same manner as in Example 6 except that the first, the second, the third, the fourth and the fifth amino acid residues from the C-terminal were replaced with lysine residue, methionine residue, glutamic acid residue, glutamine residue and tryptophan residue, respectively (SEQ ID NO. 10).

EXAMPLE 11

About 16 mg of a peptide having the amino acid sequence Lys-Thr-Arg-Arg-Trp-Gln-Trp-Arg-Met-Lys-Lys was obtained by fixing 11 amino acid residues sequentially from the C-terminal in the same manner as in Example 1 (SEQ ID NO. 11).

EXAMPLE 12

About 20 mg of a peptide having the amino acid sequence Lys-Ser-Arg-Arg-Arg-Gln-Trp-Arg-Met-Lys-Lys was obtained in the same manner as in Example 11 except that the seventh and the tenth amino acid residues from the C-terminal were replaced with arginine residue and serine residue (SEQ ID NO. 12).

EXAMPLE 13

About 17 mg of a peptide having the amino acid sequence Lys-Thr-Val-Ser-Trp-Gln-Thr-Tyr-Met-Lys-Lys was obtained in the same manner as in Example 11 except that the fourth, the fifth, the eighth and the ninth amino acid residues from the C-terminal were replaced with tyrosine residue, threonine residue, serine residue, and valine residue, respectively (SEQ ID NO. 13).

EXAMPLE 14

About 13 mg of a peptide having the amino acid sequence Lys-Thr-Phe-Gln-Trp-Gln-Arg-Asn-Met-Arg-Lys was obtained in the same manner as in Example 11 except that the second, the fourth, the fifth, the eighth and the ninth amino acid residues were replaced with arginine residue, asparagine residue, arginine residue, glutamine residue, and phenylalanine residue, respectively (SEQ ID NO. 14).

EXAMPLE 15

About 16 mg of a peptide having the amino acid sequence Lys-Thr-Lcu-Arg-Trp-Gln-Asn-Glu-Met-Arg-Lys was obtained in the same manner as in Example 11 except that the second, the fourth, the fifth and the ninth amino acid residues were replaced with arginine residue, glutamic acid residue, asparagine residue, and leucine residue, respectively (SEQ ID NO. 15).

EXAMPLE 16

Amino acid residues were sequentially fixed in the same manner as in Example 1 except for the use of Ultrosyn B resin (manufactured by Pharmacia LKB Co.). After the completion of coupling of all amino acids, the protecting group other than acetoamidomethyl were removed by means of a solvent comprising 94% trifluoroacetic acid, 5% phenol, and 1% ethandiol, and a peptide was released by the use of saturated ammonia/methanol solution. Then, the peptide was purified by high-performance liquid chromatography, concentrated and dried to obtain about 4 mg of a peptide drivative having the amino acid sequence Arg-Trp-Gln-Trp-Arg-NH$_2$ (SEQ ID NO. 16).

EXAMPLE 17

About 5 mg of a peptide derivative having the amino acid sequence Arg-Arg-Trp-Gln-Trp-Arg-NH$_2$ was obtained in the same manner as in Example 16 except that amino acid residues were fixed sequentially in the same manner as in Example 6 (SEQ ID NO. 17)

EXAMPLE 18

About 15 mg of a peptide derivative having the amino acid sequence Lys-Thr-Arg-Arg-Trp-Gln-Trp-Arg-Met-Lys-Lys-NH$_2$ was obtained in the same manner as in Example 16 except that amino acid residues were fixed in the same manner as in Example 11 (SEQ ID NO. 18 ).

EXAMPLE 19

About 9.6 kg of pet feed were produced by adding 120 mg of the antimicrobial peptide obtained by the same method as in Example 3 to 10 kg of pet feed of the following composition and uniformly mixed.

| Powdery meat | 6.0% |
|---|---|
| Fish meal | 5.0% |
| Corn | 5.0% |
| Soybean oil meal | 12.0% |
| Wheat germ | 8.0% |
| Wheat | 51.23% |
| Skim milk powder | 4.0% |
| Beef tallow | 2.0% |
| Brewer's yeast powder | 2.0% |
| Bone meal | 2.0% |
| Common salt | 0.5% |

| -continued | |
|---|---|
| Mixed vitamins and minerals | 0.27%. |

EXAMPLE 20

A skin cream of the following composition was produced by the conventional method:

| Stearic acid | 14.25% |
|---|---|
| Ethanol | 1.90% |
| Squalene | 2.85% |
| Octyldodecyl myristate | 4.75% |
| Glycerin | 9.50% |
| 1,3-butylenoglycol monostearate | 3.80% |
| Polyoxyethylene (20 mol) sorbitane | 2.85% |
| Antimicrobial peptide of Example 4 | 0.0005% |
| Purified water | 60.10% |

EXAMPLE 21

A mixture of 7.4 kg of a commercially available honey (79% sugar, 20% water and 0.2% protein), 2.6 kg of a commercially available butter (15% water) and 240 mg of an antimicrobial peptide obtained in the same manner as in Example 5 was uniformly mixed in a container while heating to 40° C., then rapidly cooled to 10° C., and whipped by stirring while blowing nitrogen gas to obtain a honey food product having plasticity in an amount of about 9.7 kg.

EXAMPLE 22

Commercially available sodium casein (manufactured by Nissei Kyoeki Co.) in an amount of 1 kg and commercially available maltodextrin (manufactured by Matsutani Chemical Co.) in an amount of 3 kg were dissolved in about 20 kg of hot water, added with minerals in a given amount, and heated to 65° C. Then, 0.5 kg of commercially available corn oil (manufactured by Taiyo Fats and Oils Co.) and 0.3 kg of commercially available coconut oil (manufactured by Taiyo Fats and oila Co.) both containing dissolved fat-soluble vitamins in a given amount were added to this solution, and the mixture was emulsified by means of a high-pressure equalizer and added with water-soluble vitamins in a given amount. An antimicrobial peptide synthesized in the same manner as in Example 6 was added in an amount of 36 mg to this emulsified solution, and the mixture was sterilized at 135° C. for two seconds, and aseptically charged into a 500 ml sterile container, to obtain 49 units of an enteral nutrient.

EXAMPLE 23

An ointment of the following composition was produced by the conventional method:

| Vaseline | 26.3% |
|---|---|
| Paraffin | 5.3% |
| Cetostearylalcohol | 2.1% |
| Propylene glycol | 10.5% |
| Polyoxyethylene polyoxypropylene Glycol ether | 3.2% |
| Antimicrobial peptide of Example 7 | 0.0005% |
| Purified water | 52.6%. |

EXAMPLE 24

An antimicrobial peptide synthesized in the same manner as in Example 8 in an amount of 140 mg was added to 10 kg of a commercially available assorted feed for adult hog of the following composition, and the mixture was uniformly mixed to obtain a hog-raising feed:

| | | |
|---|---|---|
| | Corn | 34.7% |
| | Milo | 30.0% |
| | Soybean oil meal | 9.0% |
| | Fish seal | 5.0% |
| | Wheat bran | 10.0% |
| | Alfalfa meal | 6.0% |
| | Refinery molasses | 3.0% |
| | Tricalcium phosphate | 1.1% |
| | Calcium carbonate | 0.4% |
| | Common salt | 0.4% |
| | Vitamin mixture | 0.2% |
| | Mineral mixture | 0.2% |

EXAMPLE 25

A commercially available cellulose agent "Cellulose AMANO" (manufactured by Amano Pharmaceutical Co.; cellulose saccharifying ability: 15,000 units/g; the unit is hereafter expressed as "u") in an amount of 105 g was added to 120 tons of phosphoric acid buffer solution (pH: 6.5). Then, 6.0 kg of konjak powder (manufactured by Shimizu Chemical Co.) was dissolved by stirring into the mixture while heating the same to 40° C. After holding at 40° C. for 16 hours, the mixture was heated to 95° C. for ten minutes and the reaction was stopped. The resultant solution was continuously separated centrifugally at 6,000=g, and the supernatant liquid was passed sequentially through 1,500 ml of cation exchange resin DOWEX 50W×8 (H+type; manufactured by Dow Chemical Co.) and 6,000 ml of anion exchange resin DOWEX 1×8 (OH- type; manufactured by Dow Chemical Co.), for desalting, then concentrated and spray-dried, to obtain about 4,200 g of a decomposed neutral polysaccharide.

Subsequently, 3,000 g of this a decomposed neutral polysaccharide, 57.91 g of sodium chloride (manufactured by Ishizu Co.), 2.57 g of calcium chloride (manufactured by Ishizu Co.), 1.53 g of magnesium chloride hexahydrate (manufactured by Kokusan Chemical Co.), 39.2 g of sodium lactate (manufactured by Wako Junyaku Kogyo Co.), 50 g of amino acid mixture (manufactured by Ajinomoto Co.), and 0.4 g of an antimicrobial peptide prepared in the same manner as in Example 13 were dissolved into 10 tons of water, and the resultant solution was subjected to ultrafiltration through an ultrafiltration membrane ACL-1050 (manufactured by Asahi Chemical Co.) having a differential molecular weight of 13,000, and the resultant filtrate was sterilized at 121° C. for ten minutes, thus obtaining a peritoneum dialysate which was germfree and did not contain any pyrogenic substances.

EXAMPLE 26

Sixty units of blueberry jam (sugar concentration: 50° Bx) were manufactured by mixing 4.5 kg of blueberry fruit, 4.5 kg of sugar, 0.07 kg of pectin, 0.01 kg of citric acid, 0.01 kg of sucrose ester of fatty acid (HLB: 10), and 400 mg of an antimicrobial peptide prepared in the same manner as in Example 15 with 1 kg of water, dissolving the same, sterilizing the same at 102° C. for five minutes by means of a scrubber type heat exchanger, cooling the mixture to 85° C., charging 150 g of the same into glass bottles, sealing the bottles, and cooling the same.

EXAMPLE 27

A tooth-paste of the following composition was produced:

| | |
|---|---|
| Sorbitol | 47.0% |
| Glycerin | 15.0% |
| Carboxymethylcellulose sodium | 2.0% |
| Sorbitan ester of fatty acid | 1.0% |
| Saccharin sodium | 1.0% |
| Antimicrobial peptide derivative of Example 16 | 0.002% |

EXAMPLE 28

A skin cream rinsing agent of the following composition was produced:

| | |
|---|---|
| Sodium monolauryl phosphate | 35.5% |
| Sodium monomethylphosphate | 10.0% |
| Sodium chloride | 7.0% |
| Polyethylene glycol (molecular Weight: 8,000) | 5.0% |
| Sorbitol | 5.0% |
| Aromatic | 0.7% |
| Antimicrobial peptide derivative of Example 18 | 0.002%. |

What is claimed is:

1. A substantially purified and isolated peptide having antimicrobial activity which consists of an amino acid sequence selected from the group consisting of SEQ ID Nos. 1–15, or antimicrobial derivatives thereof having minor amino acid partial substitutions or additions which do not abolish the antimicrobial properties of the peptide.

2. An antimicrobial composition which comprises an antimicrobially effective amount of at least one antimicrobial peptide which contains one or more of the amino acid sequences of SEQ ID Nos. 1–15, or antimicrobial derivatives thereof having minor amino acid partial substitutions or additions which do not abolish the antimicrobial properties of the peptide or pharmaceutically or sitologically acceptable salts thereof, or a mixture thereof, as active components.

3. The antimicrobial composition according to claim 2, wherein the at least one antimicrobial peptide, derivative, salt or mixture is present in a concentration of at least 1 micromole per kg.

4. The substantially purified and isolated peptide according to claim 1, and derivatives thereof having at least one of an amidated C-terminal or an acetylated N-terminal.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 5 amino acid residues
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:1:

```
Arg  Trp  Gln  Trp  Arg
 1                    5
```

(2) INFORMATION FOR SEQ ID NO:2:

(i) SEQUENCE CHARACTERISTICS:
        (A) LENGTH: 5 amino acid residues
        (B) TYPE: amino acid
        (C) STRANDEDNESS: single
        (D) TOPOLOGY: linear (ii) MOLECULE TYPE: peptide (iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:2:

Arg  Arg  Gln  Trp  Arg
 1                    5

( 2 ) INFORMATION FOR SEQ ID NO:3:

( i ) SEQUENCE CHARACTERISTICS:
            ( A ) LENGTH: 5 amino acid residues
            ( B ) TYPE: amino acid
            ( C ) STRANDEDNESS: single
            ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:3:

Lys Val Ser Trp Arg
1            5

( 2 ) INFORMATION FOR SEQ ID NO:4:

( i ) SEQUENCE CHARACTERISTICS:
        ( A ) LENGTH: 5 amino acid residues
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:4:

Arg Asn Met Arg Lys
1                5

( 2 ) INFORMATION FOR SEQ ID NO:5:

( i ) SEQUENCE CHARACTERISTICS:
        ( A ) LENGTH: 5 amino acid residues
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:

( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:5:

Arg  Trp  Gln  Glu  Lys
 1                    5

( 2 ) INFORMATION FOR SEQ ID NO:6:

( i ) SEQUENCE CHARACTERISTICS:
                    ( A ) LENGTH: 6 amino acid residues
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:

(B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:6:

Arg Arg Trp Gln Trp Arg
 1               5

(2) INFORMATION FOR SEQ ID NO:7:

(i) SEQUENCE CHARACTERISTICS:
        (A) LENGTH: 6 amino acid residues
        (B) TYPE: amino acid
        (C) STRANDEDNESS: single
        (D) TOPOLOGY: linear (ii) MOLECULE TYPE: peptide (iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:7:

Arg Arg Arg Gln Trp Arg
 1               5

( 2 ) INFORMATION FOR SEQ ID NO:8:

( i ) SEQUENCE CHARACTERISTICS:
        ( A ) LENGTH: 6 amino acid residues
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:8:

Lys  Thr  Val  Ser  Trp  Arg
1                       5

( 2 ) INFORMATION FOR SEQ ID NO:9:

( i ) SEQUENCE CHARACTERISTICS:
        ( A ) LENGTH: 6 amino acid residues
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:

( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:9:

Lys Arg Asn Met Arg Lys
 1                   5

( 2 ) INFORMATION FOR SEQ ID NO:10:

( i ) SEQUENCE CHARACTERISTICS:
                    ( A ) LENGTH: 6 amino acid residues
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:

( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:10:

Arg  Trp  Gln  Glu  Met  Lys
 1                       5

( 2 ) INFORMATION FOR SEQ ID NO:11:

( i ) SEQUENCE CHARACTERISTICS:
                    ( A ) LENGTH: 11 amino acid residues
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:11:

Lys  Thr  Arg  Arg  Trp  Gln  Trp  Arg  Met  Lys  Lys
 1                       5                        10

( 2 ) INFORMATION FOR SEQ ID NO:12:

( i ) SEQUENCE CHARACTERISTICS:
        ( A ) LENGTH: 11 amino acid residues
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:12:

```
Lys Ser Arg Arg Arg Gln Trp Arg Met Lys Lys
 1           5                   10
```

( 2 ) INFORMATION FOR SEQ ID NO:13:

( i ) SEQUENCE CHARACTERISTICS:
        ( A ) LENGTH: 11 amino acid residues
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:

(E) HAPLOTYPE:
                    (F) TISSUE TYPE:
                    (G) CELL TYPE:
                    (H) CELL LINE:
                    (I) ORGANELLE:

(vii) IMMEDIATE SOURCE:
                    (A) LIBRARY:
                    (B) CLONE:

(viii) POSITION IN GENOME:
                    (A) CHROMOSOME/SEGMENT:
                    (B) MAP POSITION:
                    (C) UNITS:

(ix) FEATURE:
                    (A) NAME/KEY:
                    (B) LOCATION:
                    (C) IDENTIFICATION METHOD:
                    (D) OTHER INFORMATION:

(x) PUBLICATION INFORMATION:
                    (A) AUTHORS:
                    (B) TITLE:
                    (C) JOURNAL:
                    (D) VOLUME:
                    (E) ISSUE:
                    (F) PAGES:
                    (G) DATE:
                    (H) DOCUMENT NUMBER:
                    (I) FILING DATE:
                    (J) PUBLICATION DATE:
                    (K) RELEVANT RESIDUES IN SEQ ID NO:

(xi) SEQUENCE DESCRIPTION: SEQ ID NO:13:

```
Lys  Thr  Val  Ser  Trp  Gln  Thr  Tyr  Met  Lys  Lys
 1              5                        10
```

(2) INFORMATION FOR SEQ ID NO:14:

(i) SEQUENCE CHARACTERISTICS:
                    (A) LENGTH: 11 amino acid residues
                    (B) TYPE: amino acid
                    (C) STRANDEDNESS: single
                    (D) TOPOLOGY: linear (ii) MOLECULE TYPE: peptide (iii) HYPOTHETICAL:

(iv) ANTI-SENSE:

(v) FRAGMENT TYPE:

(vi) ORIGINAL SOURCE:
                    (A) ORGANISM:
                    (B) STRAIN:
                    (C) INDIVIDUAL ISOLATE:
                    (D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(vii) IMMEDIATE SOURCE:
                    (A) LIBRARY:
                    (B) CLONE:

(viii) POSITION IN GENOME:
                    (A) CHROMOSOME/SEGMENT:
                    (B) MAP POSITION:
                    (C) UNITS:

(ix) FEATURE:
                    (A) NAME/KEY:
                    (B) LOCATION:
                    (C) IDENTIFICATION METHOD:
                    (D) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:14:

```
Lys  Thr  Phe  Gln  Trp  Gln  Arg  Asn  Met  Arg  Lys
 1              5                        10
```

( 2 ) INFORMATION FOR SEQ ID NO:15:

( i ) SEQUENCE CHARACTERISTICS:
        ( A ) LENGTH: 11 amino acid residues
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:15:

```
Lys  Thr  Leu  Arg  Trp  Gln  Asn  Glu  Met  Arg  Lys
 1              5                        10
```

( 2 ) INFORMATION FOR SEQ ID NO:16:

(i) SEQUENCE CHARACTERISTICS:
  (A) LENGTH: 5 amino acid residues
  (B) TYPE: amino acid
  (C) STRANDEDNESS: single
  (D) TOPOLOGY: linear (ii) MOLECULE TYPE: peptide (iii) HYPOTHETICAL:

(iv) ANTI-SENSE:

(v) FRAGMENT TYPE:

(vi) ORIGINAL SOURCE:
  (A) ORGANISM:
  (B) STRAIN:
  (C) INDIVIDUAL ISOLATE:
  (D) DEVELOPMENTAL STAGE:
  (E) HAPLOTYPE:
  (F) TISSUE TYPE:
  (G) CELL TYPE:
  (H) CELL LINE:
  (I) ORGANELLE:

(vii) IMMEDIATE SOURCE:
  (A) LIBRARY:
  (B) CLONE:

(viii) POSITION IN GENOME:
  (A) CHROMOSOME/SEGMENT:
  (B) MAP POSITION:
  (C) UNITS:

(ix) FEATURE:
  (A) NAME/KEY: modified site
  (B) LOCATION: 5
  (C) IDENTIFICATION METHOD:
  (D) OTHER INFORMATION: /note="Arg-NH2"

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO:

(xi) SEQUENCE DESCRIPTION: SEQ ID NO:16:

Arg Trp Gln Trp Xaa
1           5

(2) INFORMATION FOR SEQ ID NO:17:

(i) SEQUENCE CHARACTERISTICS:
  (A) LENGTH: 6 amino acid residues
  (B) TYPE: amino acid residues
  (C) STRANDEDNESS: single
  (D) TOPOLOGY: linear (ii) MOLECULE TYPE: peptide (iii) HYPOTHETICAL:

(iv) ANTI-SENSE:

(v) FRAGMENT TYPE:

(vi) ORIGINAL SOURCE:
  (A) ORGANISM:
  (B) STRAIN:
  (C) INDIVIDUAL ISOLATE:
  (D) DEVELOPMENTAL STAGE:
  (E) HAPLOTYPE:
  (F) TISSUE TYPE:

( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY: modified site
                    ( B ) LOCATION: 6
                    ( C ) IDENTIFICATION METHOD:
                    ( D ) OTHER INFORMATION: /note="Arg-NH$_2$"

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:17:

Arg  Arg  Trp  Gln  Trp  Xaa
 1                    5

( 2 ) INFORMATION FOR SEQ ID NO:18:

( i ) SEQUENCE CHARACTERISTICS:
                    ( A ) LENGTH: 11 amino acid residues
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY: modified site
                    ( B ) LOCATION: 11
                    ( C ) IDENTIFICATION METHOD:
                    ( D ) OTHER INFORMATION: /note="Lys-NH$_2$"

( x ) PUBLICATION INFORMATION:
                    ( A ) AUTHORS:

(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:18:

```
Lys Thr Arg Arg Trp Gln Trp Arg Met Lys Xaa
 1               5                   10
```